US012558650B2

(12) United States Patent
Monroy Sampieri

(10) Patent No.: US 12,558,650 B2
(45) Date of Patent: Feb. 24, 2026

(54) DEVICE FOR REMOVING VOLATILE ORGANIC COMPOUNDS

(71) Applicant: Carlos Monroy Sampieri, Veracruz (MX)

(72) Inventor: Carlos Monroy Sampieri, Veracruz (MX)

(*) Notice: Subject to any disclaimer, the term of this patent is extended or adjusted under 35 U.S.C. 154(b) by 1208 days.

(21) Appl. No.: 17/299,579

(22) PCT Filed: Dec. 14, 2018

(86) PCT No.: PCT/MX2018/000148
§ 371 (c)(1),
(2) Date: Jun. 3, 2021

(87) PCT Pub. No.: WO2020/117035
PCT Pub. Date: Jun. 11, 2020

(65) Prior Publication Data
US 2022/0032229 A1 Feb. 3, 2022

(30) Foreign Application Priority Data

Dec. 4, 2018 (MX) .................... MX/a/2018/015049

(51) Int. Cl.
*B01D 53/44* (2006.01)
*B01D 53/85* (2006.01)
(Continued)

(52) U.S. Cl.
CPC ............. *B01D 53/44* (2013.01); *B01D 53/85* (2013.01); *C12M 29/04* (2013.01); *C12M 41/26* (2013.01);
(Continued)

(58) Field of Classification Search
None
See application file for complete search history.

(56) References Cited

U.S. PATENT DOCUMENTS

2004/0137610 A1 7/2004 Park
2006/0027099 A1 2/2006 Kim
(Continued)

FOREIGN PATENT DOCUMENTS

CN 102500230 6/2012
CN 105831851 8/2016
(Continued)

*Primary Examiner* — William H. Beisner
(74) *Attorney, Agent, or Firm* — Defillo & Associates, Inc.; Evelyn A. Defillo

(57) ABSTRACT

A device for the removal of volatile organic compounds including at least one first connector arranged at the outlet of a gas stream to be treated. At its top, has a connection extension that links with the bioreactor located in the middle part of the device (having a nutrient solution where organisms that degrade volatile organic compounds can grow). Additionally, there is a dispersion arrangement that couples with an outlet through which the gaseous stream, once treated, is expelled out to the environment. A distribution network of a nutritive solution with microorganisms that degrade volatile organic compounds. The connection extension includes a distributor cone that is arranged in an inverted way and internally emptied and also has a cylindrical extension at its top. The distributor cone allows the airflow to be displaced by an external path into the internal walls of the distributor cone, whose cylindrical extension connects with a second perforated cylinder with multiples drill holes throughout its periphery. The axial axis of the cylindrical extension coincides with the axial axis of the distributor cone. The perforations of this second perforated cylinder are arranged so that the gas output can enter the bioreactor from its bottom.

18 Claims, 10 Drawing Sheets

(51) Int. Cl.
    *C12M 1/00*     (2006.01)
    *C12M 1/34*     (2006.01)
    *C12N 1/12*     (2006.01)
    *C12R 1/89*     (2006.01)

(52) U.S. Cl.
    CPC ............... *C12M 47/18* (2013.01); *C12N 1/12*
    (2013.01); *B01D 2257/708* (2013.01); *C12R*
    *2001/89* (2021.05)

(56)             References Cited

U.S. PATENT DOCUMENTS

| | | | |
|---|---|---|---|
| 2007/0048856 | A1 | 3/2007 | Parent |
| 2012/0263635 | A1 | 10/2012 | Cork |

FOREIGN PATENT DOCUMENTS

| | | |
|---|---|---|
| CN | 105879660 | 8/2016 |
| CN | 205593122 | 9/2016 |
| CN | 106268288 | 1/2017 |
| CN | 106367831 | 2/2017 |
| CN | 106512709 | 3/2017 |
| CN | 206234932 | 6/2017 |
| CN | 107051184 | 8/2017 |
| CN | 206372690 | 8/2017 |
| CN | 107158909 | 9/2017 |
| CN | 107185393 A * | 9/2017 |
| CN | 107217015 | 9/2017 |
| JP | 2016128160 | 7/2016 |
| KR | 20060109367 A * | 10/2006 |
| KR | 101353678 | 1/2014 |
| KR | 101468634 | 12/2014 |
| KR | 101696236 | 1/2017 |
| KR | 101721998 | 3/2017 |
| KR | 101738143 | 5/2017 |
| WO | WO0245826 | 6/2002 |
| WO | WO2018005052 | 1/2018 |

* cited by examiner

303

308

307

302

306

305

304

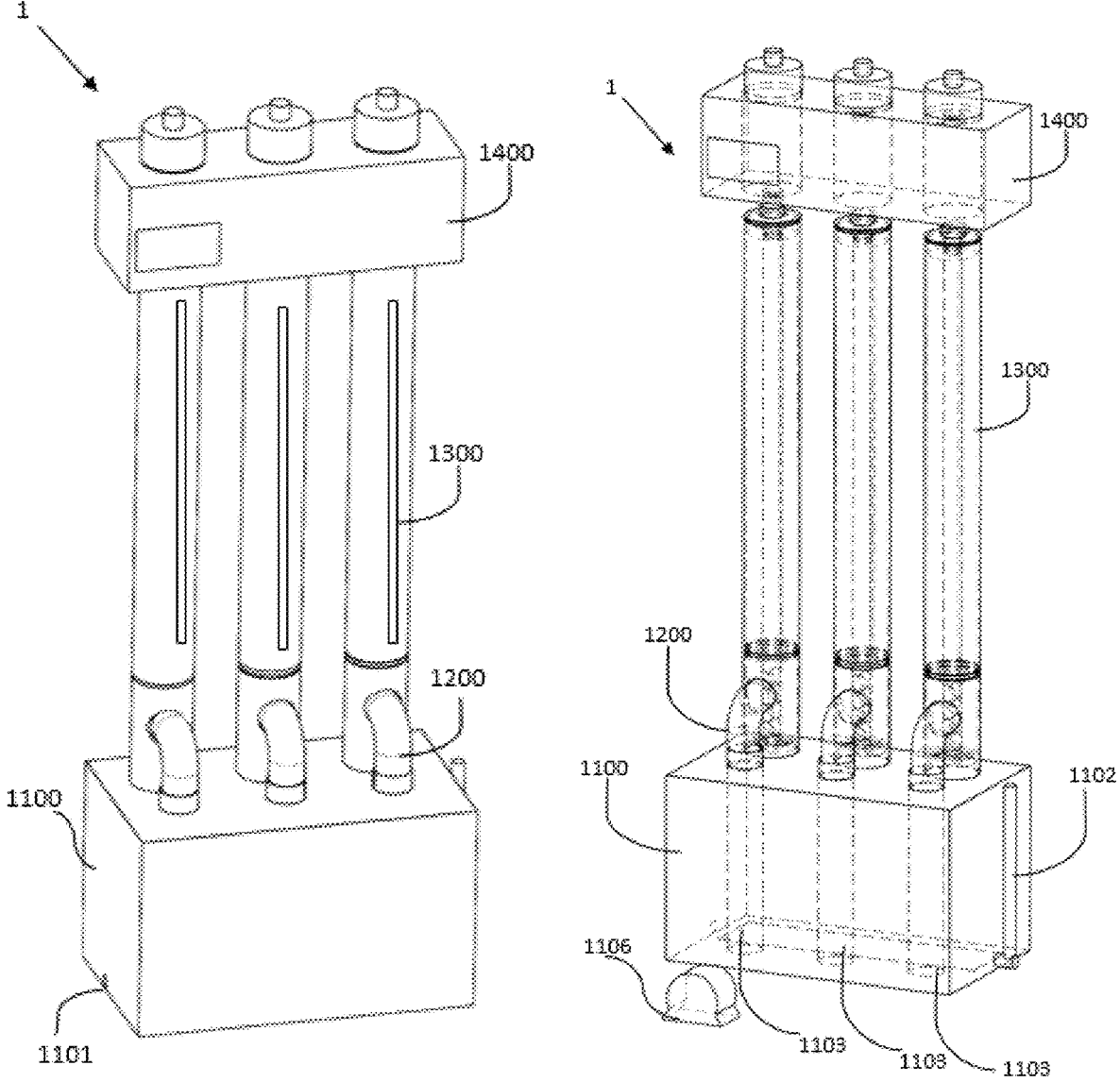
Figure 7                                    Figure 8

DEVICE FOR REMOVING VOLATILE ORGANIC COMPOUNDS

CROSS REFERENCE TO RELATED APPLICATION

This application is a national stage entry of PCT/mx2018/000148 filed Dec. 14, 2018, under the International Convention and claiming priority over Mexican Patent Application No. MX/a/2018/015049 filed Dec. 4, 2018.

TECHNICAL FIELD

The present invention belongs to the field of various industrial techniques. In particular, it belongs to the field of devices and processes used for the separation, capture and/or elimination of particles in the air, gases or vapours, even more specifically it refers to a device for the removal of volatile organic compounds.

BACKGROUND

Air pollution is an environmental problem that has gained relevance in recent years, especially in large cities. It is known that the issue and dispersion of pollutants in the atmosphere is caused by anthropic activities, in which topography and weather conditions contribute significantly. Before this problem, many countries have implemented actions to reduce the production of atmospheric pollutants, such as the Kyoto Protocol, an agreement signed by industrialized and developing countries in Dec. 11, 1997, which promotes sustainable development. The signatory countries are obliged to comply with the quantified commitments in order to limit and reduce emissions, and to apply and develop policies and measures in tandem with their national circumstances. The signatory countries are committed to reduce their GHG emissions by 5% with respect to their emissions in the base year (1990), from 2005 to 2012. Among the implemented measures, there is the control of pollution in vehicles, which has been successful in reducing three pollutants that are part of the group of pollutants defined by the United States Environmental Protection Agency (USEPA) as criteria pollutants: lead (Pb), carbon monoxide (CO) and sulphur dioxide (SO2).

However, the permissible limits of air quality standards for other pollutants are being exceeded frequently. Regarding environmental pollution, the one related to volatile organic compounds (VOC's) plays a central role. In general, the term VOC refers to those volatile organic compounds that produce a negative effect on the environment, even in small concentrations of parts per million (ppm). The term VOC encompasses all volatile organic compounds that are able to produce photochemical oxidants due to reactions caused by sunlight in presence of nitrogen oxides. VOC includes a wide variety of organic compounds, such as aromatic, aliphatic, hydrocarbons, halogenated, aldehydes, ketones, alcohols, glycols, ethers, phenols, and others, which make up the majority of hazardous compounds in the air.

Due to a continuous increase in emissions, several methods have been developed in order to remove VOC's, especially in industrialized countries, where legislative restrictions have hardened. For instance, the international application WO 2018005052 (A1) describes a catalyst composition, catalyst devices, and methods for removing formaldehyde, volatile organic compounds and other pollutants from the air. The catalyst composition includes manganese oxide; and optionally, one or more alkali metals, alkaline earth metals, zinc, iron, binder, an inorganic oxide or carbon. A further instance is the Chinese application CN107158909 (A) related to a removal device and method of volatile organic compounds for industrial waste gases. The method includes the next stages: waste gas pre-treatment, high silicon molecular sieve adsorption, ozone oxidation and withdrawn of remaining liquid and purified gas.

Korean patent KR 101468634 (B1) refers to a volatile organic compound and bad smell removal system that uses an electrostatic precipitator, which has an improved ozone generating function and a low temperature adsorbing oxidant catalyst. The system has; on one hand, a pre-treatment tank for electrostatic precipitation, where fine particles (such as tar, mist, dust. etc.) are processed. On the other hand, it accounts with a catalyst tank with a low-temperature adsorbent catalyst, which allows decomposing the residual ozone that passes through the pre-treatment tank while achieving to adsorb, de-sorb, and oxidize volatile organic compounds and bad smells.

The US application US 2012263635 (A1) refers to a device for removing one or more volatile organic compounds from a gas stream. The device has, on one hand; a conduit with thermic means in order to perform a pre-heating stage, in which the temperature of the gas stream is increased by heat transfer; and, on the other, a combustion chamber that forms a combustion zone, which has a fluid connection with the conduit.

Drawn upon the aforementioned, it can be summarized that VOC removal technologies have been focused on upgrading thermal oxidation reactors, catalysts, condensers, absorbents, adsorbents, and membrane separation processes, among others. Currently, the global trend is focused on the usage of environmentally friendly technologies, which consider the use of microorganisms for the removal of VOC's. Such is the case of the Korean application KR 101353678 (B1), which refers to a bio-filter that eliminates the causes of bad smell and volatile organic compounds with an integrated treatment device. The bio-filter can effectively provide the nutrient source and life circumstances required by microorganisms by using porous tubes. Moreover, if a cage filled with a polyurethane foam carrier conveyor is used, the microorganisms' fixation rate increases while avoiding pressure phenomena, which improves durability and the ability to remove bad smell. Another application where microorganisms are considered for VOC removal is the Chinese utility model application CN206372690 (U), which refers to a treatment device that retains volatile organic compounds, which includes: a filter equipment; a circulation cistern; an inlet for remaining gas; a circulation pump and a water nozzle. A pipeline and a filter chamber connect with the gas outlet of the circulation cistern. The middle part of the chamber has the filter's medium material; and the top end of the chambers' filter is equipped with a subtraction fan and a washing device with a washing chamber. The model reveals that a microorganism degrades remaining gas containing volatile organic compounds, which are managed through filtration and washing stages.

The state of the art is robust in this field. Other applications that consider the use of microorganisms for the removal of volatile organic compounds are: CN107217015 (A), CN107051184 (A), KR101738143 (B1), CN206234932 (U), KR101721998 (B1), CN106512709 (A), CN106367831 (A), KR101696236 (B1), CN106268288 (A), CN205593122 (U), CN105879660 (B), CN105831851 (A), JP2016128160 (A), to say a few.

However, none of the previous focuses on reducing the VOC's that are issued by fuel supply stations, which are an important source of pollution in cities, many of which account with official standards to regulate this type of atmospheric pollutants.

In this way, there still is a need to find a solution to the problem of removing or regulating the emissions of volatile organic compounds in fuel supply stations (especially those located in urban areas or open public places), which could allow for the removal of such pollutants more efficiently.

THE OBJECT OF THE INVENTION

The object of protection is a device for the removal of volatile organic compounds that accounts with at least a first connector arranged at the outlet of a gas stream to be treated, which at its top part has a connection extension to link with the bioreactor (that is located in the middle part of the device) that contains a nutrient solution where organisms that degrade volatile organic compounds can grow. At its top, there is a dispersion arrangement coupled to an outlet through which the treated gaseous stream is released to the environment. It also accounts with a distribution network for the nutritive solution with microorganisms. The connection extension has a distributor cone that is; arranged in an inverted way; it is internally emptied; and it has a cylindrical extension at its top. The distribution cone allows the airflow to be displaced by an external route into the internal walls of the distributor cone, which connects with a second perforated cylinder that has numerous drill holes throughout its periphery, where its axial axis coincides with the axial axis of the distributor cone. The perforations of this second cylinder are arranged so that the gas can enter the bioreactor through its bottom.

The objectives of the present invention referred to above (and others not mentioned), will be evident in the description and the figures (developed for illustrative and non-limiting purposes) which are presented below.

BRIEF DESCRIPTION OF THE FIGURES

FIG. 7. Isometric view of a modality of the device of the invention.

FIG. 8. Isometric view in transparency of a modality of the device of the invention.

Figures 9, 10:
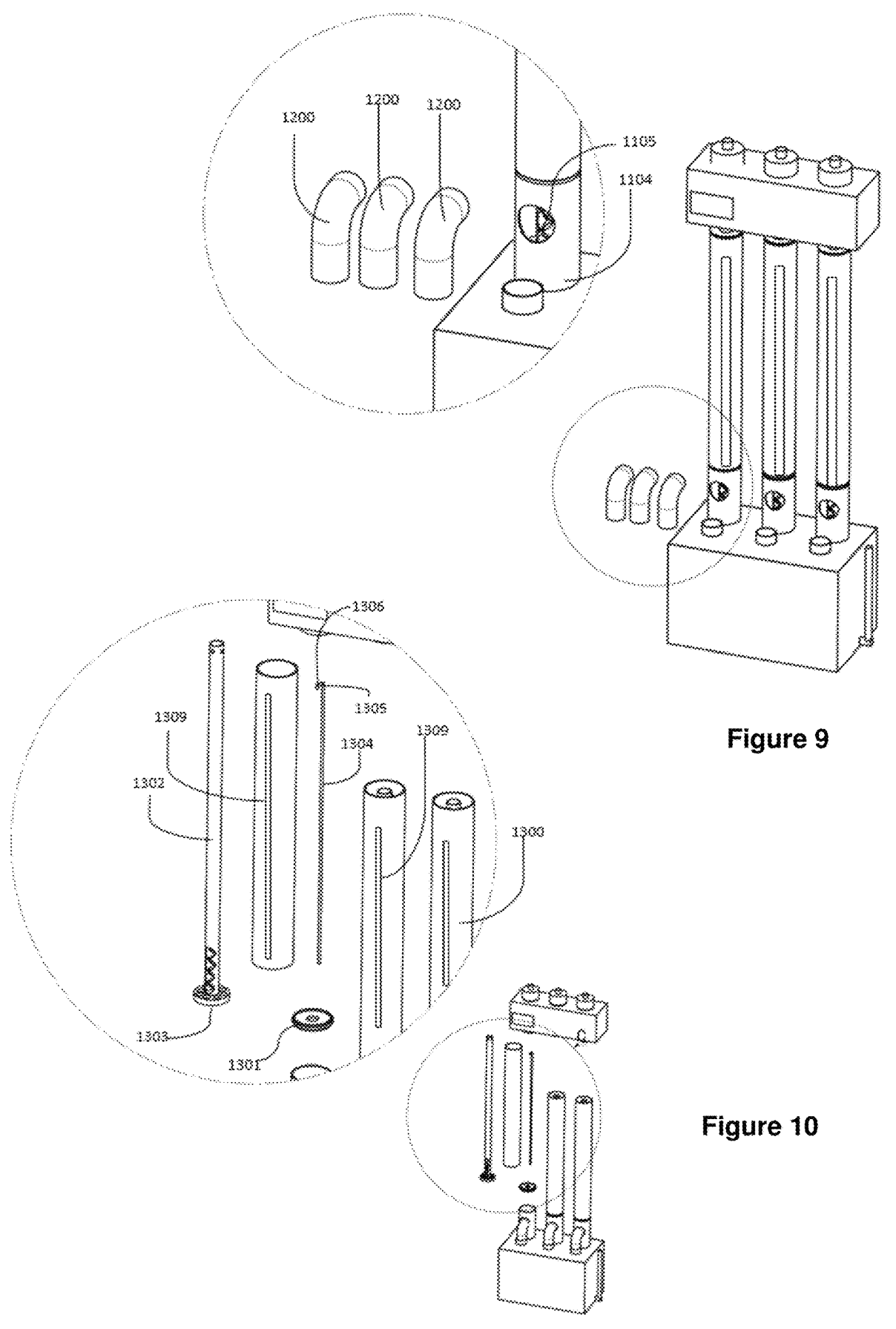

FIG. 9. Isometric view of a modality of the device of the invention with a close-up of the connectors.

FIG. 10. Isometric view of a modality of the device of the invention with a close-up of the parts that make up the exchange tank in explosive view.

DESCRIPTION OF THE INVENTION

Figure 1:
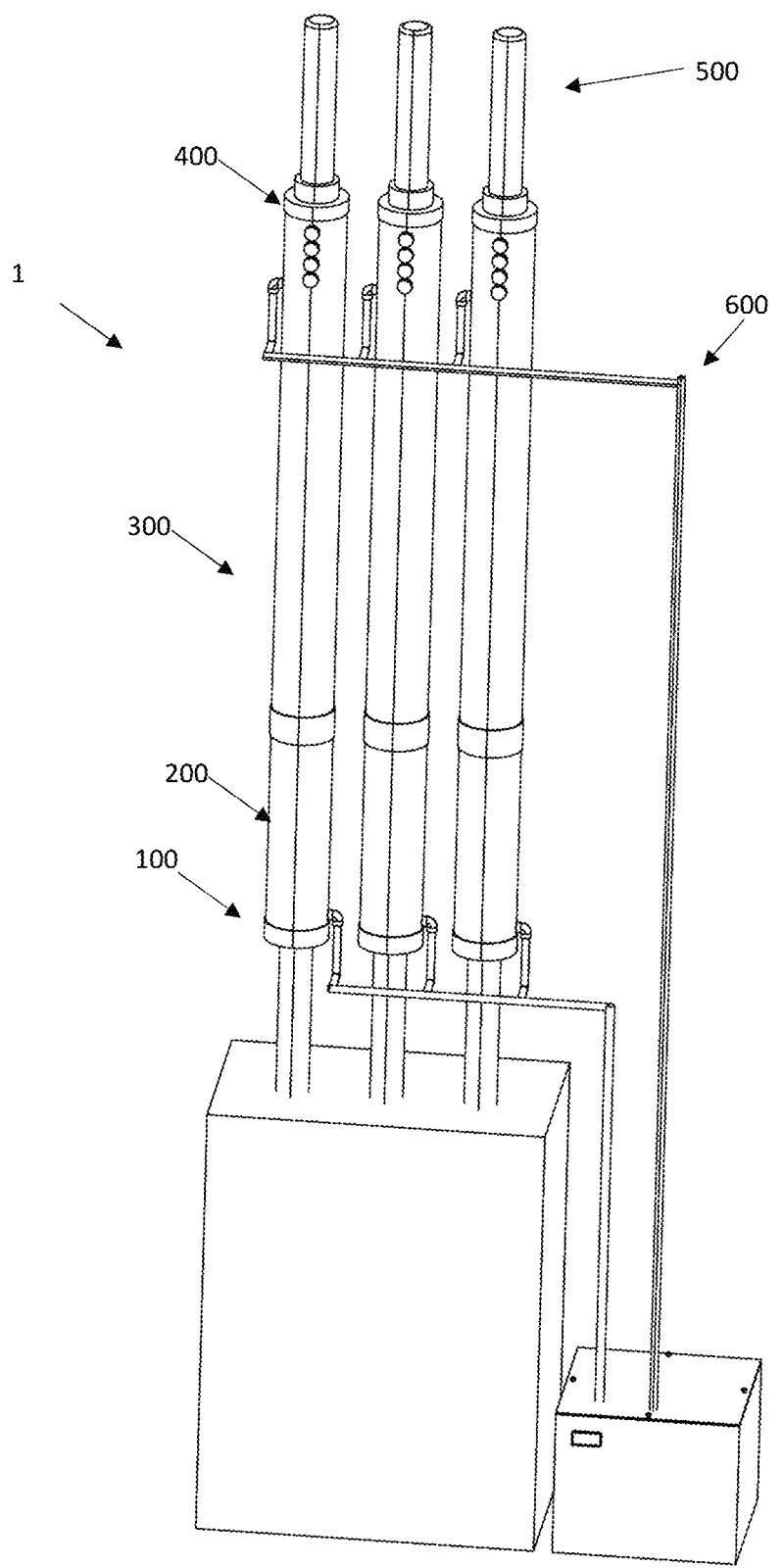
FIG. 1. Isometric view of the VOC removal device.
Figure 2:
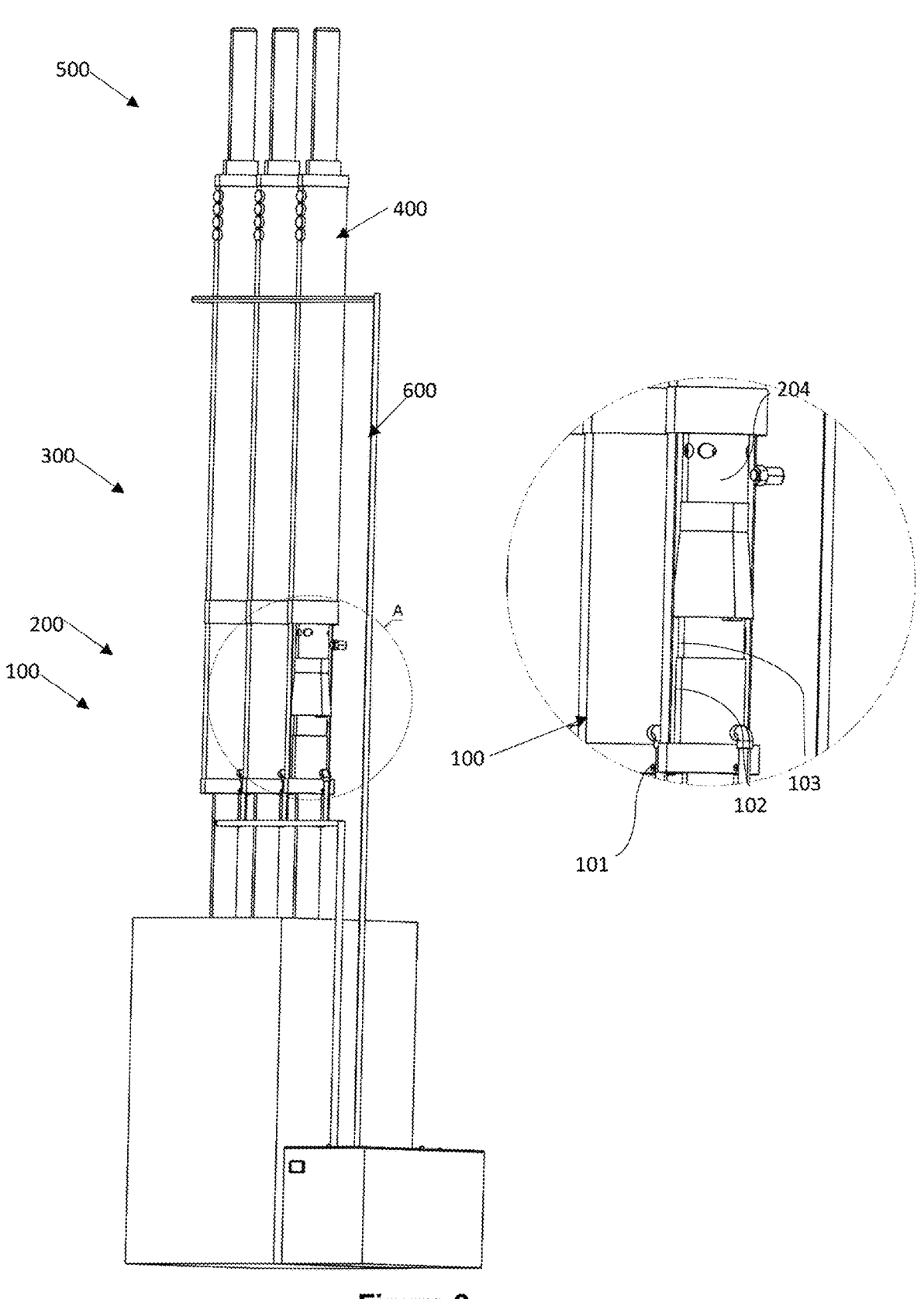
FIG. 2. Isometric view of the VOC removal device, with an enlargement of the first connector (100).
Figure 3:
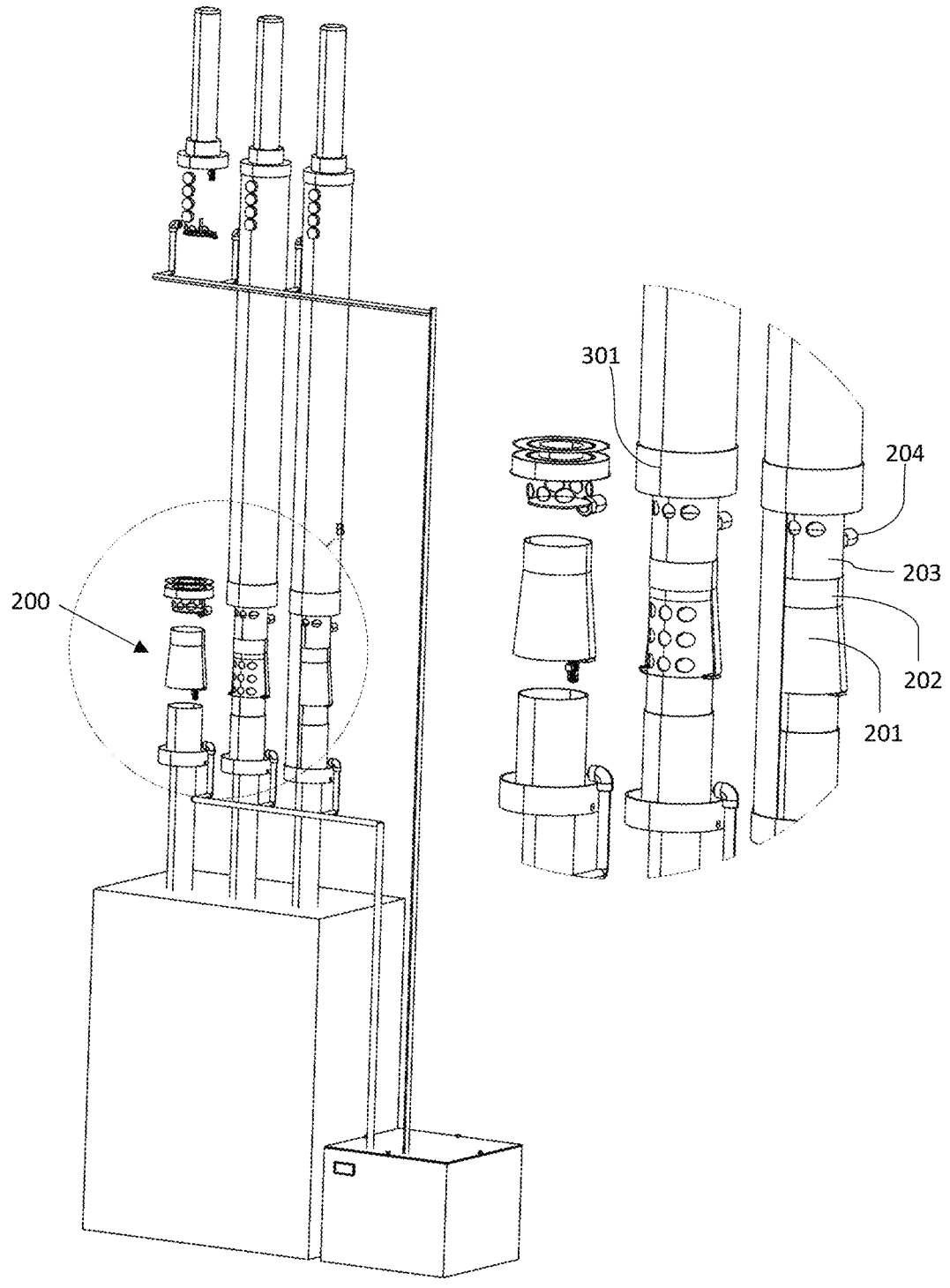
FIG. 3. Isometric view of the device for VOC removal, with an enlargement of the connection extension (200).
Figure 4:
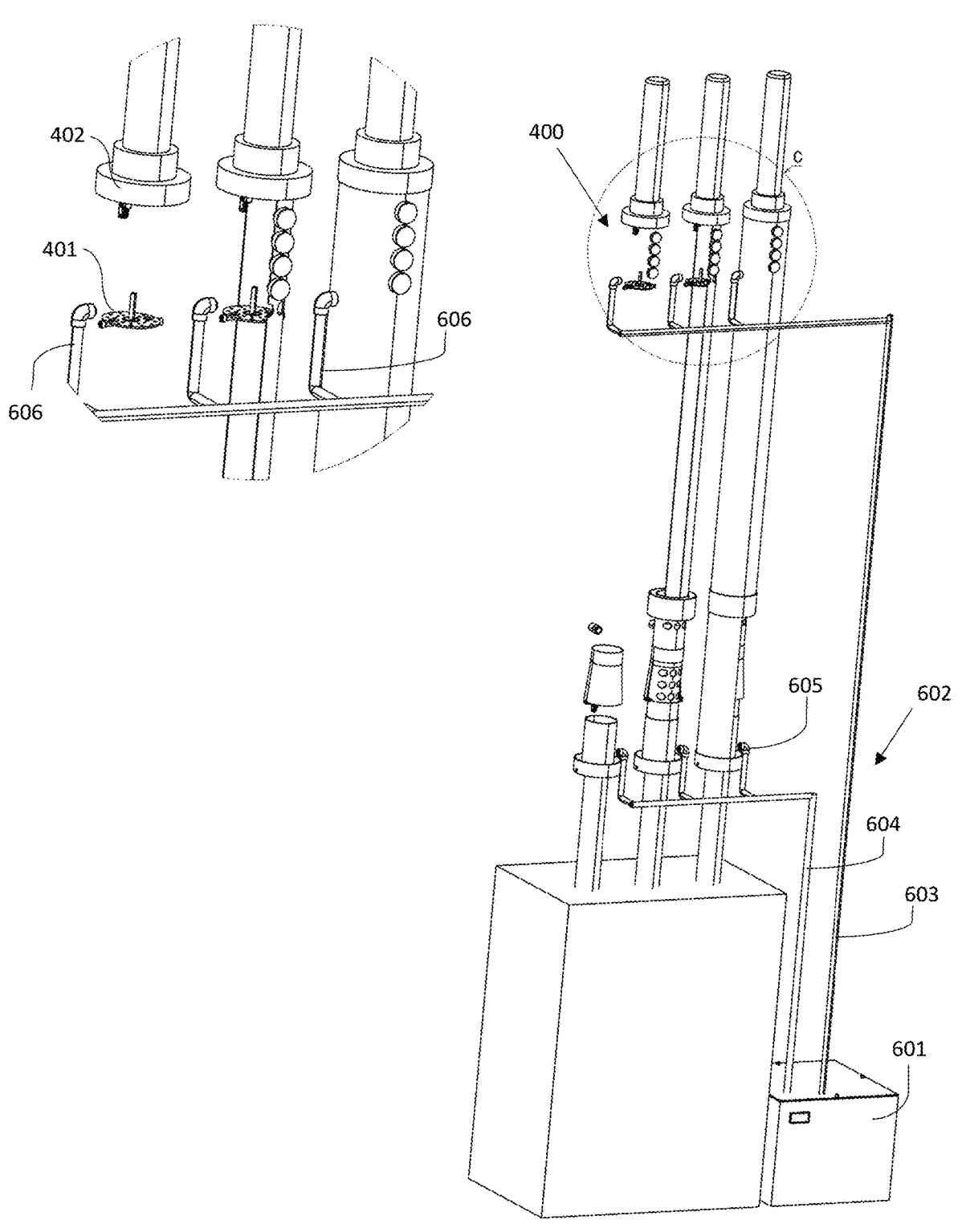
FIG. 4. Isometric view of the VOC removal device with an enlargement of the dispersion arrangement (400).
Figure 5:
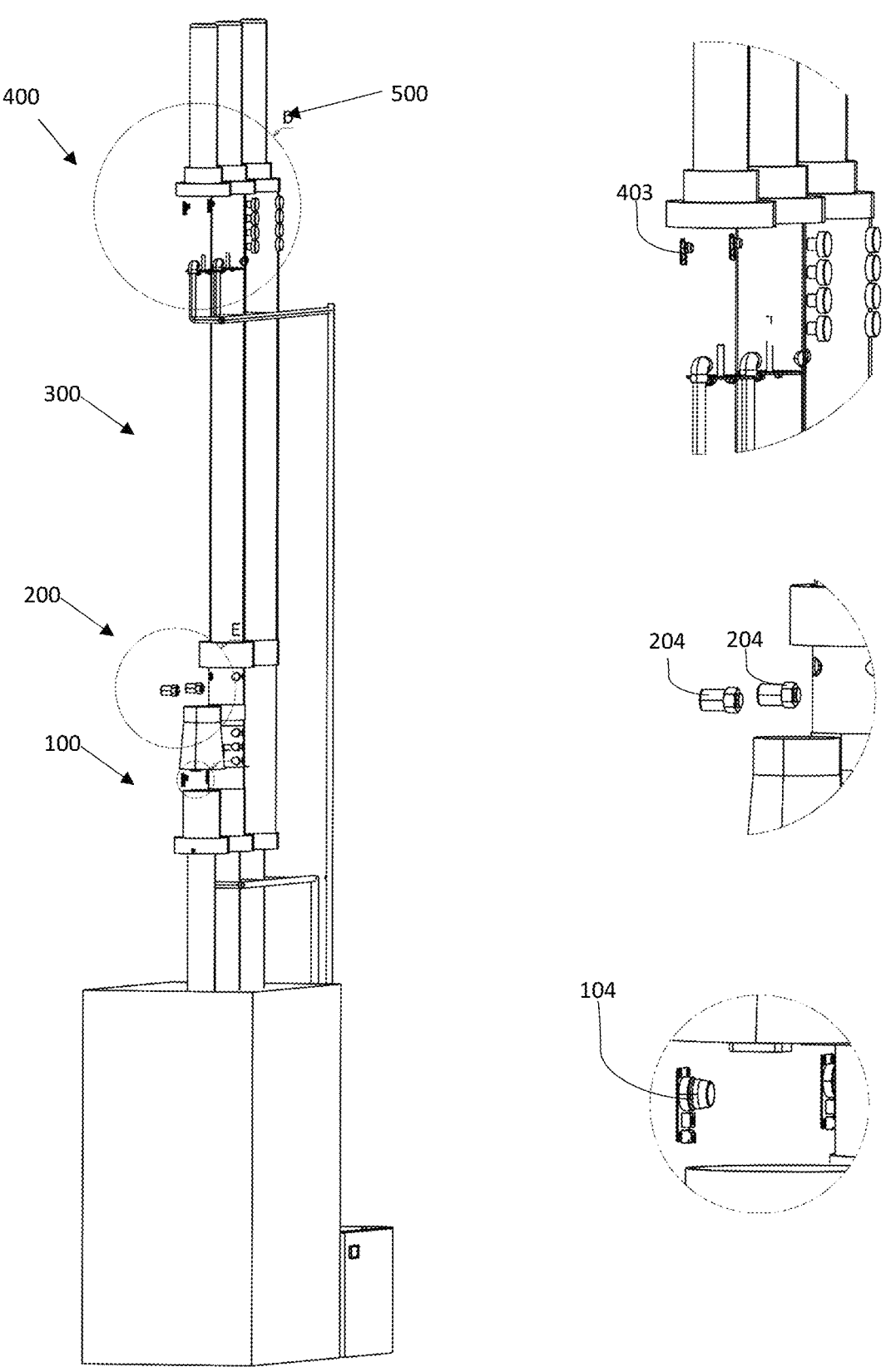
FIG. 5. Isometric view of the device for VOC removal, with an enlargement of the sensors (104 and 403) for volatile organic compounds and check valve (204).
Figure 6:
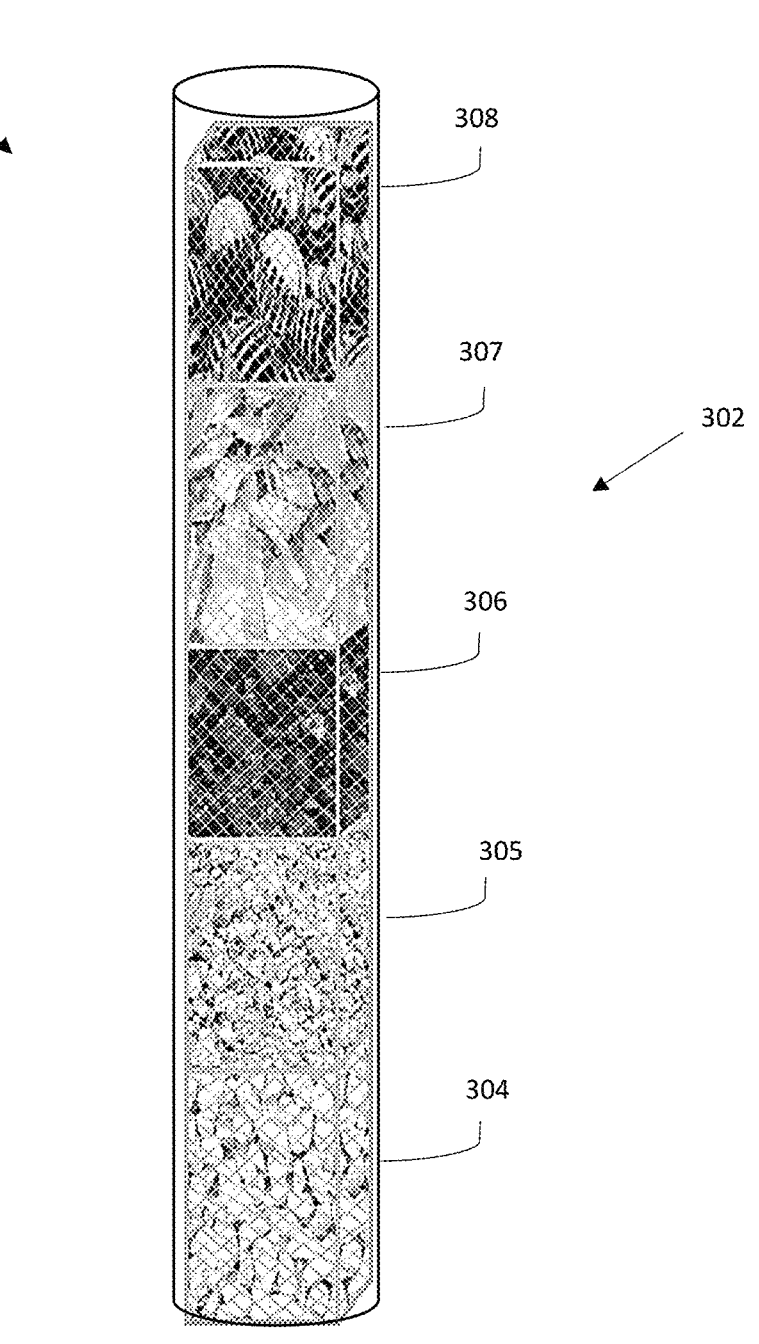
FIG. 6. Isometric view of the bio-filter (303).
Figures 11, 12:
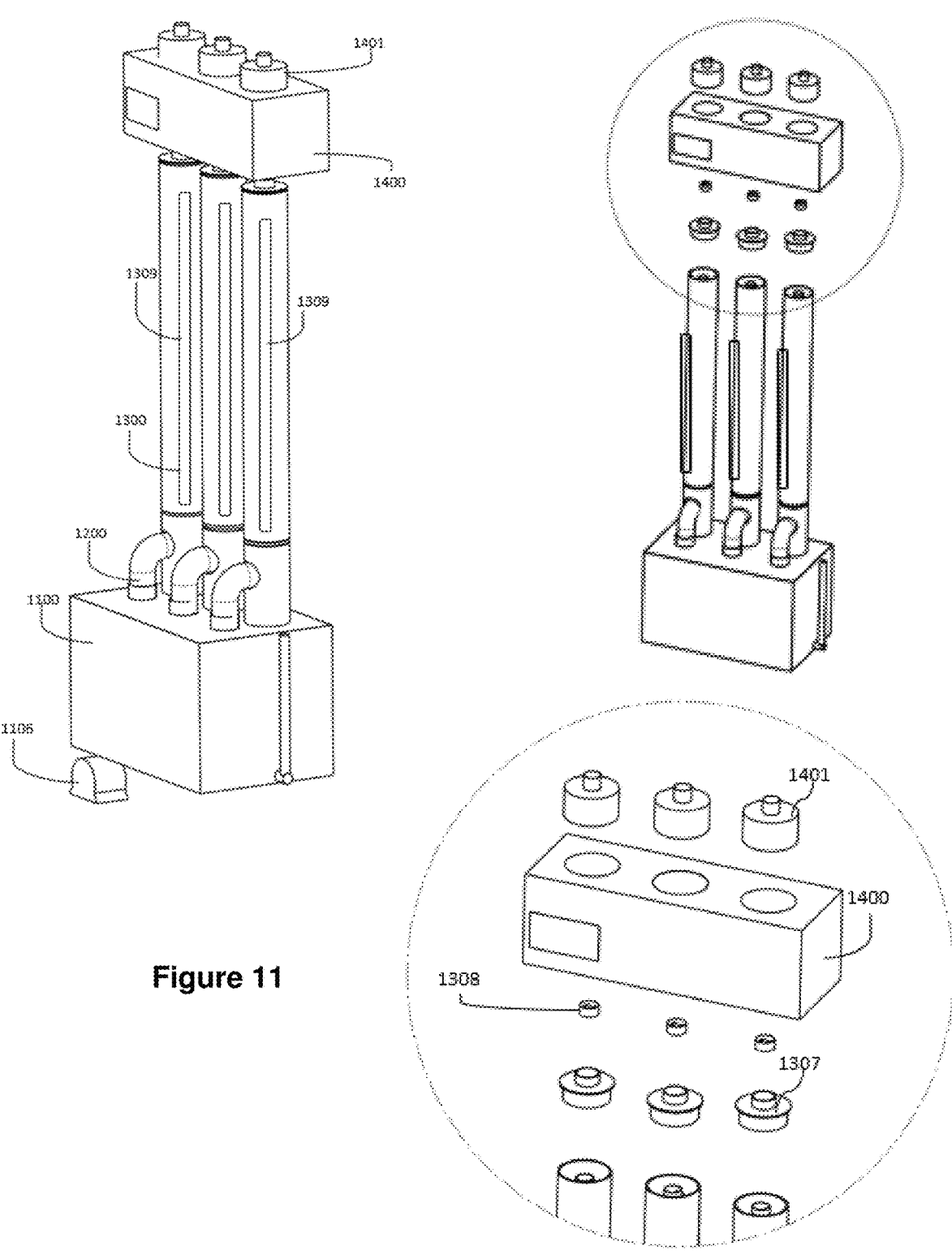
FIG. 11. Side view of a modality of the device of the invention.
FIG. 12. Isometric view of a modality of the device of the invention with a close-up of the ejection chamber.
Figure 13:
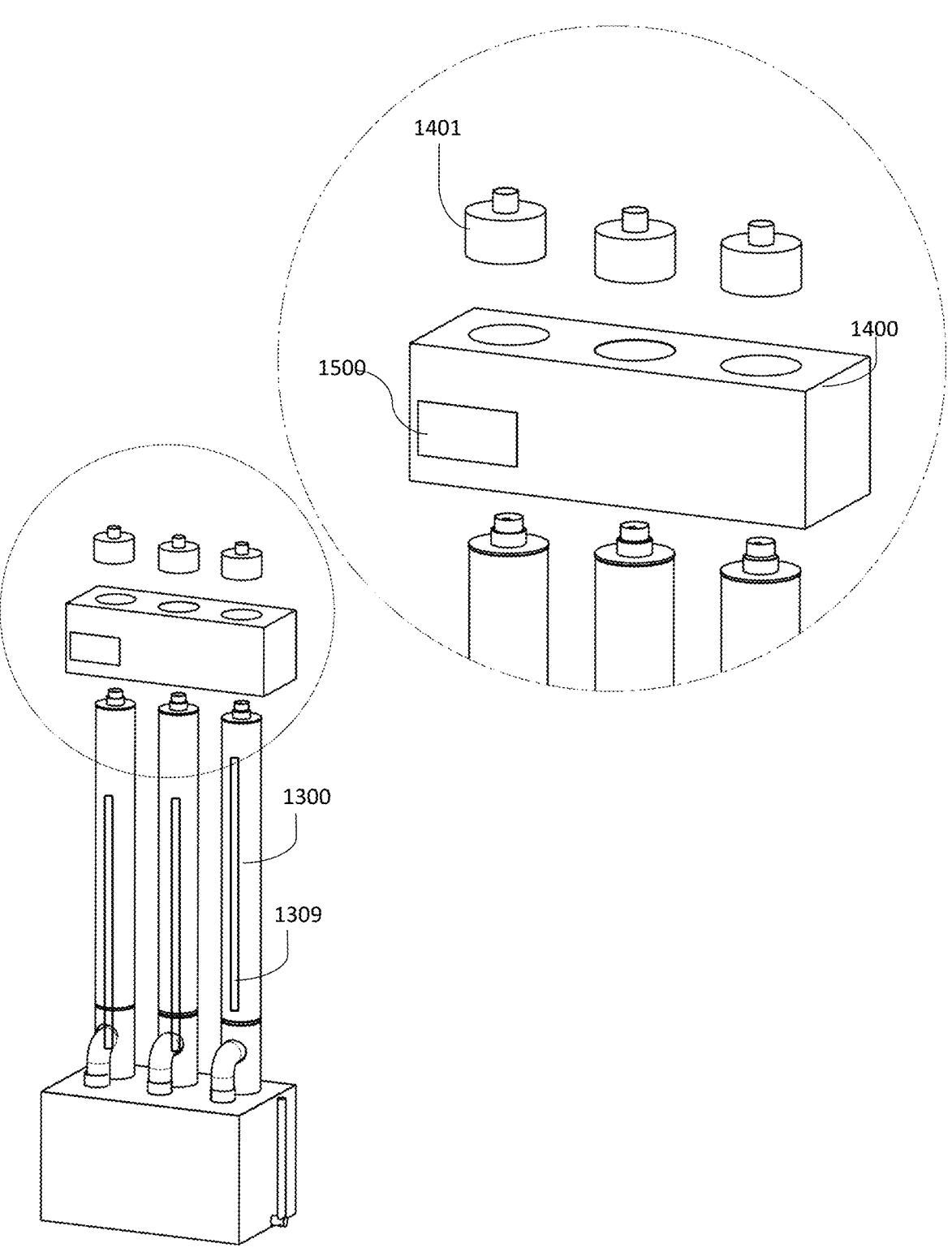
FIG. 13. Isometric view of a modality of the device of the invention with a close-up of the ejection chamber.

The present invention refers to a device for the removal of volatile organic compounds (1), which is specifically designed to be placed at the outlet conduit of a hydrocarbon tank or cistern at fuel supply stations, which (generally speaking) at least has one conduit (usually identified by its colour) depending on the type of fuel contained by the tank. The device is arranged at the outlet of the tanks to remedy the gas stream coming from inside the tank or cistern through a first connector (100). At its top part, it has a connection extension (200) that links the bioreactor (300) that is located in the middle part of the device (which contains a nutrient solution where organisms that degrade volatile organic compounds can grow). At the top part, there is a dispersion arrangement (400); and it accounts with an outlet (500) through which the gaseous stream, once treated, is expelled out to the environment with a considerable reduction of VOC's. The latter results from the biochemical processes triggered by microorganisms once they are in contact with the polluted fluid. Such microorganisms are present in a nutrient solution supplied by a distribution network (600).

The first connector (100) is placed immediately at the output of a gas expulsion conductor (which expels gas from a hydrocarbon tank or cistern). It has a circular cross section (preferably) with a first seal (101) available on its periphery, which is preferably made of a metallic material that isolates the contents of the tank's exhaust gases, and which channels the latter to a rise cylinder (102), which is higher than the size of the first seal and which coincides with its axial axis. At the top part of the rise cylinder (102) there is a first perforated cylinder (103), which has an emptied cylindrical body with a recess that is similar to that of the rise cylinder (102) and the first seal (101). It has numerous holes on its surface that allow the gas to leave the tank, and in this way to pass through the connection extension (200) towards the bioreactor (300). Likewise, the first connector (100) is the part where the nutrient solution with microorganisms re-enters to a storage tank with the nutrient solution (601), such recirculation being needed to take advantage of the microorganisms. The mentioned return occurs by gravity, and it requires an outlet connector (604) that is connected perpendicularly at the first connector's periphery (100). The first connector (100) has a first sensor (104) that allows quantifying and monitoring the amount of volatile organic compounds that are processed by the device.

The connection extension (200) is located at the top part of the first connector (100) and it has a distributor cone (201) with a truncated conical shape, which is arranged in an inverted way and internally emptied. It also has a cylindrical extension (202) at its top. The distributor cone (201) prevents the fluid of the nutrient solution with microorganisms from entering the hydrocarbon storage tank or cistern (which would alter their composition) while allowing the air flow to be displaced by an external route into its internal walls, and to be deposited into the storage tank with nutrient solution (601). The distributor cone (201) surrounds the perforated cylinder (103) at its conical part, while the cylindrical extension part (202) connects with a second perforated cylinder (203) that has numerous holes on all its periphery, and whose axial axis coincides with the axial axis of the distributor cone (201). The perforations of this second perforated cylinder (203) are arranged so that the gas output of the tank can enter the bioreactor (300) through its bottom. At the backside of the connection extension (200) there is a check valve (204) that completely closes the passage of the gaseous fluid that circulates from the connection extension (200) to the filtering tank (300) for its remediation, especially in case the pressure inside the connection extension exceeds 2.8 kgf/m2.

The bioreactor (300) has a cylindrical and internally emptied shape, which is preferably made of a polymeric material. At its bottom, it has a connection gasket (301), which has a cylindrical shape that interacts with the top part of the connection extension (200), and which subjects the bioreactor from its bottom (300). The bioreactor contains a nutrient solution where bio-remediating organisms can grow. Such organisms are selected among microorganisms, fungi, plants, the enzymes derived from them or a combination of them, which take advantage of contaminants as a source of nutrients and as natural condition. That is to say, they transform various polluting compounds such as carbon monoxide, nitrogen oxides, and Particulate Matter (10 and 2.5) into oxygen and biomass.

The degradation of the VOC's is carried out inside the bioreactors (300). Degradation-bioremediation is the process that uses microorganisms, fungi, plants or the enzymes derived from them to take a polluted environment back to its natural condition. Bioreactors, which are necessary to keep microalgae alive, store a watery solution, preferably with microalgae and/or photosynthetic cyanobacteria. One of the most necessary elements for the growth of microorganisms are nutrients in solution rich in carbon and nitrogen. In respect to the present invention, the source of nutrients is obtained by the VOC's, which mainly contain carbon, which comes from the outlet of the hydrocarbon tanks The nutrient solution can be selected according to the requirements of the species of microalgae or cyanobacteria placed inside the bioreactors (300). On the other hand, the species must be considered in order to define the composition of the cultivation medium. For example, some species like Tetraselmiss sp., Chlamydomonas sp., and Nannochloris sp. need less than fifteen % of $CO_2$ to grow, while species such as Scenedesmus sp. and *Cyanidium caldarium* tolerate concentrations from 80% to 100% respectively. The bioreactors of the present invention preferably contain any of the following types of microalgae and/or cyanobacteria: *Synechocystis, Spirulina, Dunaliella, Chlorella, Tetraselmis; Chlamydomonas, Nannochloris, Scenedesmus, Cyanidium, Anabaena, Nostoc*, combinations of these, which can be monocultures or polycultures, or any other of commercial interest.

In still another modality of the invention, the bioreactors (300) may contain a culture of microalgae and/or cyanobacteria that is native to the place where the device of the present invention is installed. This has the end to optimize the control resources of growth parameters. Autochthonous species are selected based on their high capacity to resist high concentrations of VOC's or other polluting agents, as well as for tolerating the weather conditions of the installation place.

The selection of the species to be cultivated may depend on the way in which the resulting biomass will be re-used afterwards. Biomass may be used for cosmetic, food, agronomic or any other known ends.

In addition, the bioreactors (300) can comprise a pH sensor (not shown) that is in communication with a control and monitoring module (not shown), which identifies when the pH parameter falls outside the configured range, and sends a signal for a dispenser (not shown) to provide a base or alkaline solution, which allows to stabilize the configured range again. Furthermore, each bioreactor (300) may have a temperature sensor that is in communication with the monitoring and control module.

The production of microalgae or cyanobacteria increases proportionally with temperature until reaching the optimum temperature for each species. Above the optimum temperature, breathing increases and photorespiration reduces overall productivity. The appropriate temperature may be different between species. The device preferably should comprise temperature control and monitoring means such as water sprinklers or a solar collector.

In one aspect of the invention, each bioreactor (300) can be made of a strong material. Either of some metal or transparent material to receive light, preferably acrylic with a thickness of 6 inches, which favours temperature control.

In another aspect, the bioreactors (300) contain filtering material (302), which provides the advantage to have a bio-filter (303) that improves the absorption of gases and the regeneration of the liquid phase simultaneously.

Bio-filters are made up of columns packed with filtering material (302) that allow the development of a biofilm that favours the increase in volumetric cell density. The specific area of the package (the contact area per unit volume of column) is adequate to avoid both, pressure drop in the column, and the risk that the emptied place could be obstructed by microbial growth.

In bio-filters (303), the polluted water passes through the filtering material (302) with a porous surface, which is where microorganisms develop. Volatile organic compounds are transferred to this wet biofilm to be eventually transformed into O2, which is taken to the outlet (500). The device of the present invention allows to achieve high rates of degradation. The filtering materials (302) can be land, different types of compost, wood waste, peat, sugar cane waste, peanut shells, vermiculite, perlite, ceramic materials, and activated carbon. These filtering materials (302) normally contain enough minerals to sustain a suitable population.

The filtering material (302) of the bio-filters (303) may preferably consist of a first package (304) of coarse porosity stone; a second package (305) of medium side porosity stone; a third package (306) of activated carbon; a fourth organic bed packing (307); and a fifth package (308) of bio-spheres. Such packages are held in place, preferably by retention meshes at the periphery of the space to be contained.

The dispersion arrangement (400) is located at the top part of the bioreactor (300); It is integrated by a distributor plate (401) that has a circular shape; it is supported by at least four supporting means placed on the upper internal wall of the filtering tank (300), and it has numerous holes on its surface, which allow to pass the nutrient solution through the bioreactor (300) and to spill the former inside the latter. The dispersion arrangement is fed by an outlet connection (603) of the distribution network (600), which is linked to the dispersion arrangement through a lateral perforation. At its top, the dispersion arrangement has an output connector (402) in which the outputs that indicate the content of each tank or cistern are connected. At the backside of the dispersion arrangement (400), there is a second sensor (403) that censuses and monitors the amount of VOC's that are taken out of the device through the output after the treatment received.

The distribution network (600) has the role to supply the nutritive solution (where organisms that degrade volatile organic compounds grow) to the different points required by the device, such as the connection extension (200), the filtering tank (300) or the dispersion arrangement (400). It is mainly made up of a storage tank with nutrient solution (601); it contains a hydraulic pump (not shown) of at least ¼ hp; and it has a removable cover that has a pair of outlet means (602), one of which is the connection mean for an outlet connection (603), and the other is for a return connection (604). The first of these extends to the area of the dispersion array (400) and has three inlet distributors (605) that are inserted on the lateral middle zone of the dispersion arrangement (400). On the other hand, the return connection is inserted at the bottom part of the connection extension (200), and it has three return distributors (606) that collect the nutrient solution once it has passed through the bioreactor (300) and interacted with the gaseous stream coming from (for example), a hydrocarbon tank or cistern.

In a preferred modality of the invention, the nutrient solution storage tank (601) may be illuminated inside by at least one light emitting medium (not shown).

In a preferred modality, the outlet (500) has a filtering media (not shown), which allows additional purification if necessary. Such filtering media can be, for example, activated carbon, zeolites, cellulose fibres, foam, folded paper, crossed fiberglass, fibres charged for retention of dust or any other material designed for retention of polluting compounds.

One modality of the invention refers to a device for the removal of VOC's (1), which is to be installed at the outputs or terminals of hydrocarbon tanks, and which is integrated to a collection and storage container (1100), which is located at its bottom. Commonly, the latter should account with a preferably rectangular cross-section with numerous connectors at its top (1200), that interrelate with at least one bioreactor (1300), which is connected with an expulsion chamber (1400) from its top.

The collection and storage container (1100) has a rectangular cross section. At its bottom, it connects with the outlet of a hydrocarbon tank. On one of its lateral faces, the storage container preferably has a circular drilling (1101) with a shape that allows its contents to be emptied, which facilitates the maintenance of the device.

At the opposite end, there is a vertically arranged cylindrical verification unit (1102), in which is possible to see the filling level of a nutrient solution for microorganisms (preferably microalgae or cyanobacteria) inside the collection and storage container (1100). So one can identify when partial emptying occurs inside, where there is a hydraulic pump (1106), which is interrupted by at least three inlet holes (1103) that transport VOC's through tubes that longitudinally traverse the container. Such tubes have a cylindrical shape and are arranged in an area next to the front face of the collection and storage container (1100). Their centres are aligned in an axial plane with the top face of the container. In a similar way, in an area next to the top part of the inlet holes (1103), there are at least three tank bases (1104) of preferably circular cross-section that have a circular drilling (1105) on their surface. The connectors (1200) have a circular cross-section that has a bend in an area next to its middle part.

Multiple bioreactors (1300), which are located at the top part of the collection and storage container (1100), are interconnected with the reservoir bases (1104). They have a cylindrical configuration, and in their internal periphery, they have multiple light emitters (1309), preferably LED strips that can provide approximately 3,000 lumens of white light in periods of between 8 to 12 hours. The light is directed towards the solution contained by the bioreactors (1300). Light intensity is one of the main parameters to consider in a culture, because, in the absence of limitation by nutrients, photosynthesis increases with higher light intensity, until reaching the maximum specific growth rate for each species in the light saturation point. By crossing the latter, the point of photo-inhibition is reached, which can cause harmful results for the cell itself and even death, which implies a loss of photosynthetic efficiency and productivity of the culture. Therefore, the power supply for the operation of the strips, which have plurality of light emitting diodes (1309), is fixed through a power supply source (not shown).

In a modality of the present invention, it is considered that the electrical supply may consist of an energy source obtained with multiple solar panels that capture the energy contained in solar radiation, which is transformed into electrical energy. The solar panels connect to a bank of batteries whose units are preferentially arranged at the bottom part of the device. Its function is to store the charge from the solar panels, to then be connected to a current inverter, which transforms the direct current electrical energy from the solar panels into alternating current electrical energy, which is the power source for a hydraulic pump; a control and monitoring module (1500); and multiple strips of LED lights (1309).

The power supply can be provided through a connection with the distribution lines of the local power supply company. Another modality considers the possibility of supplying energy by means of an electric generator destined to the transformation of magnetic flux into electricity by means of electromagnetic induction that generates a direct current, which can be done with bicycles adapted for this purpose.

The bioreactors (1300) have a first coupling mean (1301) at their bottom, which has a part of a circular shape polymeric material that fits with the top part of the corresponding tank base (1104) and with the bottom part of the corresponding exchange tank. At its central part, the first coupling mean (1301) has a drilling that allows fluid communication between the bioreactor (1300) and the collection-storage container (1100). Inside each bioreactor (1300), there is an internally emptied spill column (1302) with a spill plate (1303) at its bottom, which is perpendicular to the axial axis of the spill column (1302), and which has multiple holes on its surface, which allow microorganism's nutritive solution to recirculate towards the collection and storage container (1100). In addition, there are also a plurality of drill holes in the lower surface of the spill column (1302). On each of the external walls of the bioreactors (1300), there is a main conductor (1304) preferably of circular cross-section, which at its top edge has a bend (1305) with an angle of 45° with respect to the axial axis of the exchange tank, which in turn has a second bend (1306) of 45° with respect to the first bend (1305), which allows to discharge the nutrient solution driven by the hydraulic pump (1106) into the collection and storage container (1100). At the top part of each of the bioreactors (1300), there is a second coupling mean (1307) with a cylindrical shape, which is coupled (through a drill hole located on its central part) with the top periphery of the spill column (1302).

In addition, the second coupling mean (1307) connects to a gaseous stream collector (1308) made up of multiple blades that assist in the process of moving a gaseous stream inside the spill column (1302).

Bioremediation is carried out in the bioreactors (1300). Bioremediation is the process that uses microorganisms, fungi, plants or the enzymes derived from them to return polluted environments to their natural condition. The bioreactors contain a watery solution with microalgae and/or cyanobacteria, which should remain alive during the device's operation One of the most necessary elements for the growth of microorganisms are nutrients (in solution) rich in carbon and nitrogen. In respect to the present invention, the source of nutrients is obtained with the VOC's (which mainly contain carbon) which enter through the inlet holes (1103) attached to the outlets of the hydrocarbon tanks of fuel supply stations.

The production of microalgae or cyanobacteria increases proportionally with temperature until reaching the optimum temperature for each species. Above the optimum temperature, breathing increases and photorespiration reduces overall productivity. The appropriate temperature may be different between species. The device preferably should comprise temperature control and monitoring means such as water sprinklers or a solar collector. In addition, each bioreactor (1300) should be preferably made of a transparent material that allows light, preferably acrylic with thickness of 6 inches, which favours temperature control.

The ejection chamber (1400), which has a rectangular cross section, is arranged at the top part of the multiple bioreactors (1300) and interconnects with both, (the bottom part of) the second coupling mean (1307), and with a plurality of outlet means (1401), which in turn align with multiple drill holes at the top part of the ejection chamber. The outlet means (1401), which have a cylindrical shape, are the final element by which a gaseous stream gets into and outside of the pollutant's collector device (1).

In another aspect of the invention, it is considered that, a control and monitoring module (1500) may consist in a power source, a programmable logic card and a set of relays connected to sensors, which measure various chemical-physical parameters. The monitoring module controls the hydraulic pump, the lights and the general operational conditions of the device with the following logic programming:

The logic programming that determines the functionality of the device is reactive to the data monitored through various sensors. For example, light intensity in the LED light strips, sensors of physical-chemical parameters and pH.

The activation of the LED light strips for supplying the light energy actives as a function of radiation in real time, which is monitored through a luminosity sensor (under certain lumens over time).

The hydraulic pump is activated based on the concentrations found in the fluid that contains the VOC's, which are measured by the physical-chemical sensors.

The widely described VOC's removal device offers the advantage of comprising bioremediators in situ, under favourable operating conditions independently of seasonal variation (preferably in fuel supply stations). Other advantages include the ease of harvesting biomass, the maintenance of the culture of microorganisms without contamination, and control and monitoring of the cultivation conditions, which finally have an impact on the desired conditions at the same time while reducing operating costs.

Although the foregoing description was developed taking into account the preferred modalities of the invention, it should be noted by those skilled in the art that any modification of shape and detail will be within the spirit and scope of the present invention. The terms in which this report has been written, should always be taken into a broad and non-limiting sense. The materials, shape, and description of the elements will be susceptible to variation as long as it does not imply an alteration of the essential features of the model.

The invention claimed is:

1. A device for the removal of volatile organic compounds comprising:
    at least one first connector (100) arranged at an outlet of a gas stream to be treated;

a connection extension (200) having a first end connested each one of the at least one first connector (100);
    a bioreactor (300) having a first end connected to a second end of the connection extension (200), the bioreactor contains a nutrient solution where organisms that degrade volatile organic compounds grow;
    a dispenser (400) having a first end connected to second end of the bioreactor;
    an outlet (500) coupled to the dispenser;
    a distribution device (600) connected to a second end of the dispenser (400), the distribution device (600) contains a nutritive solution with microorganisms that degrade volatile organic compounds;
    wherein the connection extension (200) includes a distributor cone (201) arranged in an inverted way, a hollow body, and a cylindrical extension (202) connected to the distribution cone (201);
    wherein the distributor cone (201) moves an airflow into internal walls of the distributor cone (201);
    wherein the cylindrical extension (202) connects with a first perforated cylinder (203), the perforated cylinder includes multiples drill holes throughout its periphery;
    wherein an axial axis of the cylindrical extension coincides with an axial axis of the distributor cone (201).

2. The device for the removal of volatile organic compounds according to claim 1, wherein the first connector (100) has a circular cross-section and a first seal (101) on a periphery,
    wherein the first connector (100) isolates exhaust gases and moves the exhaust gases to a riser cylinder (102),
    wherein the riser cylinder (102) has a size that is greater than a size of the first seal,
    wherein a second perforated cylinder (103) is connected to the riser cylinder (102), the second perforated cylinder (103) has a hollow cylindrical body with a recess and a plurality of holes on a surface.

3. The device for the removal of volatile organic compounds according to claim 1, wherein the first connector (100) has a first sensor (104) that senses and monitors the amount of VOC's entering the device.

4. The device for the removal of volatile organic compounds, according to claim 3, wherein the dispenser (400) includes a second sensor (403) that senses and monitors the amount of volatile organic compounds being expelled out from the device after treatment.

5. The device for the removal of volatile organic compounds according to claim 1, wherein the connection extension (200) includes a check valve (204).

6. The device for the removal of volatile organic compounds according to claim 1, wherein the bioreactor (300) has a cylindrical shape and at a bottom end has a connection gasket (301) that interacts with the top part of the connection extension (200).

7. The device for the removal of volatile organic compounds according to claim 1, wherein a nutrient solution of the bioreactor (300) contains organisms with capacity to bio-remediate contaminated streams having a microorganism selected from the group consisting of fungi, plants or the enzymes derived from them, or combinations.

8. The device for the removal of volatile organic compounds according to claim 1, wherein the bioreactor (300) contains a monoculture or polyculture of microalgae and/or cyanobacteria selected from the group consisting of *Tetraselmis, Chlamydomonas, Nannochloris, Scenedesmus, Cyanidium, Synechocystis, Spirulina, Dunaliella, Chlorella, Tetraselmis*, Chlamyadomonas, Nannochloris, *Scenedesmus, Anabaena, Nostoc*, and combinations thereof.

9. The device for the removal of volatile organic compounds, according to claim 8, wherein the monoculture or polyculture of microalgae and/or cyanobacteria is an autochthonous species.

10. The device for the removal of volatile organic compounds according to claim 1, wherein the bioreactor (300) has:

a pH sensor that communicates with a controlling and monitoring module, which identifies when the pH parameter falls outside the configured range and sends a signal for a dispenser to provide a base or alkaline solution, which allows to stabilize the parameter again; and/or a temperature sensor that communicates with the module.

11. The device for the removal of volatile organic compounds according to claim 1, wherein the bioreactor (300) contains a filtering material (302) for the development of a microbial film that favors the increase in volumetric cell density, which allows to obtain a bio-filter (303) for both, the absorption of gases, and the regeneration of the liquid phase.

12. The device for the removal of volatile organic compounds according to claim 11, wherein the filtering material (302) is selected among land, compost, wood waste, peat, cane bagasse, peanut shells, vermiculite, perlite, ceramic materials, activated carbon, or combinations thereof.

13. The device for the removal of volatile organic compounds according to claim 11, wherein the filtering material (302) includes a first packing (304) of coarse porosity stone; a second packing (305) of medium porosity stone; a third packing (306) of activated carbon; a fourth organic bed packing (307); and a fifth packing (308) of biospheres.

14. The device for the removal of volatile organic compounds according to claim 1, wherein the dispenser (400) includes:

in a circular shape distributor plate (401), at least four support devices to support the distributor plate (401), the at least four devices are placed at the top part of an inner wall of the bioreactor (300), multiple drill holes on a surface, which allow the nutrient solution to pass and to be spilled into the interior of the bioreactor (300), and an outlet connector at a top end of the dispersion arrangement (402).

15. The device for the removal of volatile organic compounds according to claim 1, wherein the distribution device (600) includes a storage tank (601) containing a nutrient solution; a hydraulic pump in an internal part and a removable cover on the top, a first outlet device and a second outlet device (602), the first outlet device is connected for an outlet connection (603), and wherein the second outlet device is connected to a connection return (604);

wherein the second outlet device is connected to the dispenser (400) and includes three income distributors (605); wherein the return connection return is inserted into a bottom part of the connection extension (200), and includes three return distributors (606) that collect the nutrient solution once it has passed through the bioreactor (300) and interacted with the gaseous stream to be treated.

16. The device for the removal of volatile organic compounds; according to claim 15, wherein the storage tank with nutrient solution (601) is internally illuminated by at least one light-emitting medium.

17. The device for the removal of volatile organic compounds, according to claim 1, wherein the outlet (500) has a filtering media, which is selected from the group consisting of activated carbon, zeolites, cellulose fibers, foam, folded paper, crossed fiberglass, fibers charged for dust retention, and combinations thereof.

18. The device for the removal of volatile organic compounds according to claim 1, wherein the device is coupled to an output of an outlet conduit of a hydrocarbon tank or a cistern of fuel supply stations.

* * * * *